United States Patent [19]

Kanner

[11] Patent Number: 5,324,305
[45] Date of Patent: Jun. 28, 1994

[54] BIOADHESIVE APPLICATOR

[75] Inventor: Rowland W. Kanner, Guntersville, Ala.

[73] Assignee: Ryder International Corporation, Arab, Ala.

[21] Appl. No.: 990,453

[22] Filed: Dec. 15, 1992

[51] Int. Cl.⁵ .............................................. A61B 17/00
[52] U.S. Cl. ..................................... 606/213; 606/93; 401/2; 222/146.2; 222/146.5
[58] Field of Search ........................ 606/27, 92, 93, 94, 606/213, 214; 401/1, 2; 219/229; 222/146.2, 146.5; 226/127, 166, 126, 164

[56] References Cited

U.S. PATENT DOCUMENTS

| | | | |
|---|---|---|---|
| 3,232,509 | 2/1966 | Newton | 226/127 |
| 3,364,577 | 1/1968 | Oakleaf et al. | 219/229 |
| 3,430,816 | 3/1969 | Nadherny et al. | 222/146.5 |
| 4,065,034 | 12/1977 | Callan | 222/146.5 |
| 4,067,481 | 1/1978 | Feldman | 222/146.5 |
| 4,122,850 | 10/1978 | Bucalo | 219/229 |
| 4,553,935 | 11/1985 | Ueno | 222/146.5 |
| 4,938,388 | 7/1990 | Yeh | 401/2 |
| 5,026,187 | 6/1991 | Belanger et al. | 222/146.5 |
| 5,061,178 | 10/1991 | Ueno | 222/146.5 |
| 5,108,403 | 4/1992 | Stern | 606/94 |

Primary Examiner—Stephen C. Pellegrino
Assistant Examiner—Jeffrey A. Schmidt
Attorney, Agent, or Firm—Trexler, Bushnell, Giangiorig & Blackstone, Ltd.

[57] ABSTRACT

A bioadhesive applicator is disclosed in the present invention that allows a user to easily spread a melted adhesive material over a surface area surrounding an incision in an eye after a surgery thereby sealing the incision. The applicator generally includes a housing, a heat sink and tip assembly and a cartridge assembly. The cartridge assembly includes an adhesive material and a plunger assembly for advancing the adhesive material into the heat sink. The heat sink and tip assembly is attached to the front of the housing for melting and dispensing the material onto the surface area of the incision.

13 Claims, 2 Drawing Sheets

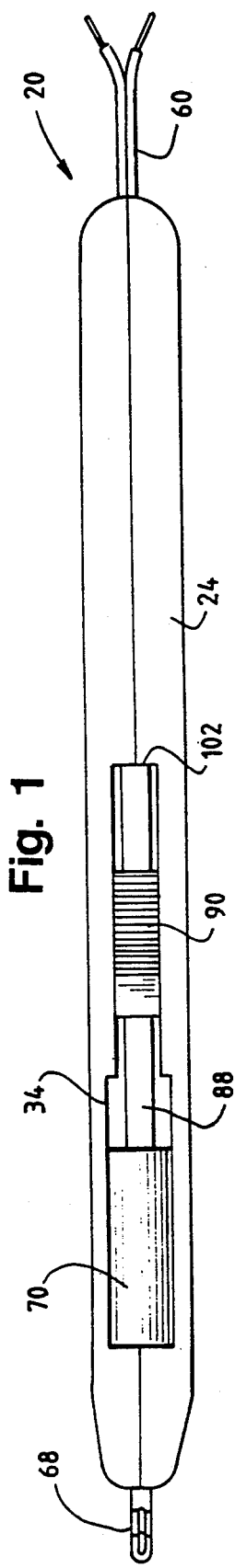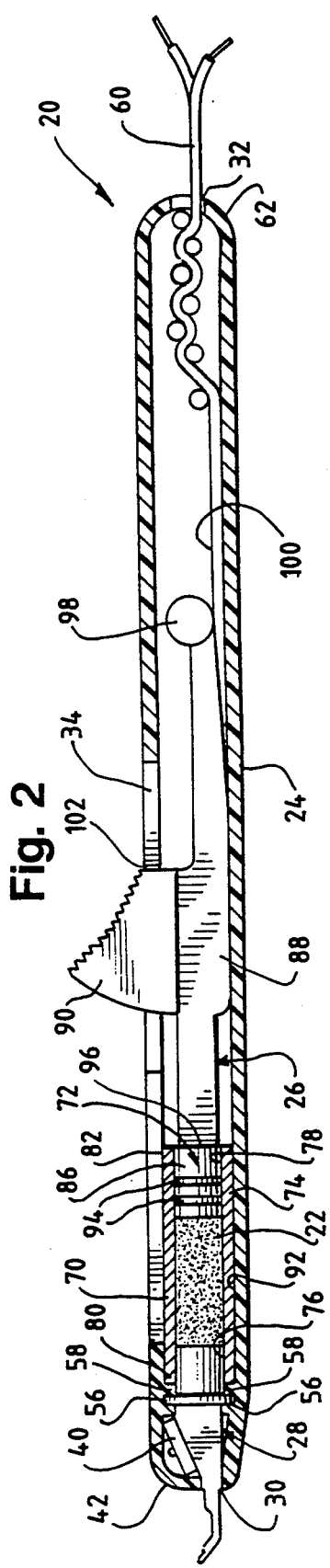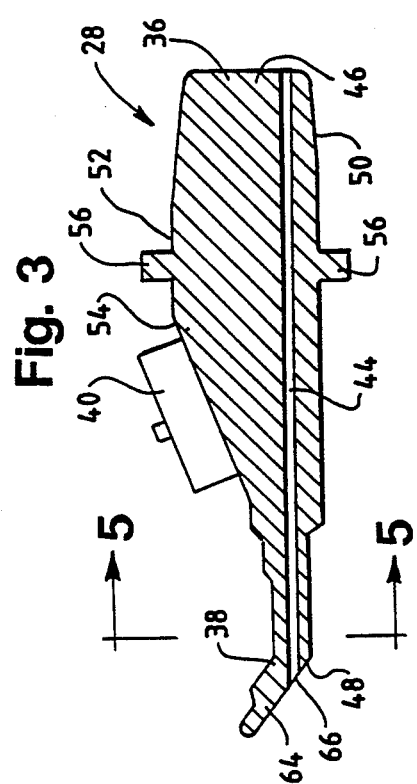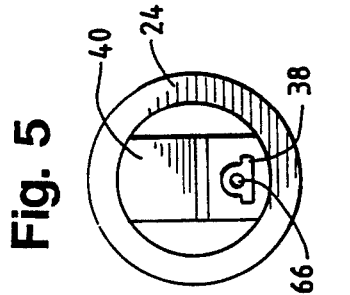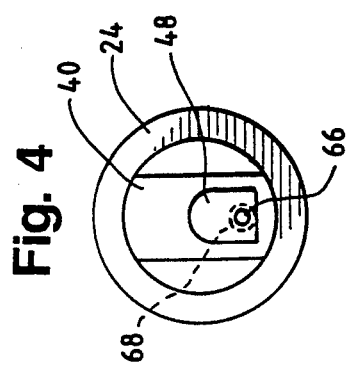

BIOADHESIVE APPLICATOR

BACKGROUND OF THE INVENTION

The present invention is directed to a bioadhesive applicator that dispenses a bioadhesive material in liquid form onto a surface area of an incision in order to bond the incision. A typical application for the bioadhesive applicator would be to bond a cornea/sclera incision commonly made for interocular (IOL) lens insertion or replacement.

Prior art techniques have relied upon sutures to close the IOL incision. However, these sutures often lead to scarring and discomfort. In order to remedy this problem, cyanoacryite glues or adhesives have been employed. However, these glues bond instantly and lack the open time needed by a surgeon for adjusting the incised tissue to a proper desired location before the adhesive sets.

Preferably, the adhesive should be applied along a 0.120–0.190 inch width and 0.002 inch thickness in order to properly seal the incision. However, problems arise in that the viscous bioadhesive has a very rubbery consistency even upon melting and tends to reform immediately after extrusion into a bead of approximately 0.018 inch thickness.

The present invention presents a novel bioadhesive applicator and adhesive cartridge assembly that is intended to overcome many of these prior art problems as well as to present several other advantages and improvements over the prior art procedure and techniques.

OBJECTS AND SUMMARY OF THE INVENTION

A general object of the present invention is to provide a novel bioadhesive applicator and adhesive cartridge for dispensing a bioadhesive material for sealing an incision after surgery.

Another object of the present invention is to provide a bioadhesive applicator that allows a user to easily and quickly assemble the applicator components for use.

It is a further object of the present invention to provide a disposable bioadhesive applicator that allows a user to easily spread melted adhesive over a surface area surrounding an incision.

Briefly, and in accordance with the foregoing, the present invention comprises a bioadhesive applicator for allowing a user to easily spread a melted bioadhesive material over a surface area of an incision after a surgery, such as IOL eye surgery, thereby sealing the incision. The applicator generally includes a housing, a heat sink and tip assembly and a cartridge assembly. The cartridge assembly includes the adhesive material and a plunger member for pressurizing and advancing the adhesive material into engagement with the heat sink and into a dispensing bore in the heat sink. The heat sink and tip assembly is attached to the front of the housing and includes a spatula-like applicator tip for spreading the bioadhesive material onto the surface area of the incision.

BRIEF DESCRIPTION OF THE DRAWINGS

The organization and manner of the structure and operation of the invention, together with further objects and advantages thereof, may best be understood by reference to the following description, taken in connection with the accompanying drawings, wherein like reference numerals identify like elements in which:

FIG. 1 is a top view of a bioadhesive applicator according to the present invention;

FIG. 2 is a partial sectional side view of the bioadhesive applicator according to the present invention in the fully assembled condition;

FIG. 3 is a sectional view of a heat sink and tip assembly according to the present invention and also illustrates the placement of the heater unit on said heat sink;

FIG. 4 is a front end view of the bioadhesive applicator according to the present invention;

FIG. 5 is a cross sectional view of FIG. 3 taken along line 5—5 of FIG. 3;

DETAILED DESCRIPTION OF THE PREFERRED EMBODIMENT

Figure 6:
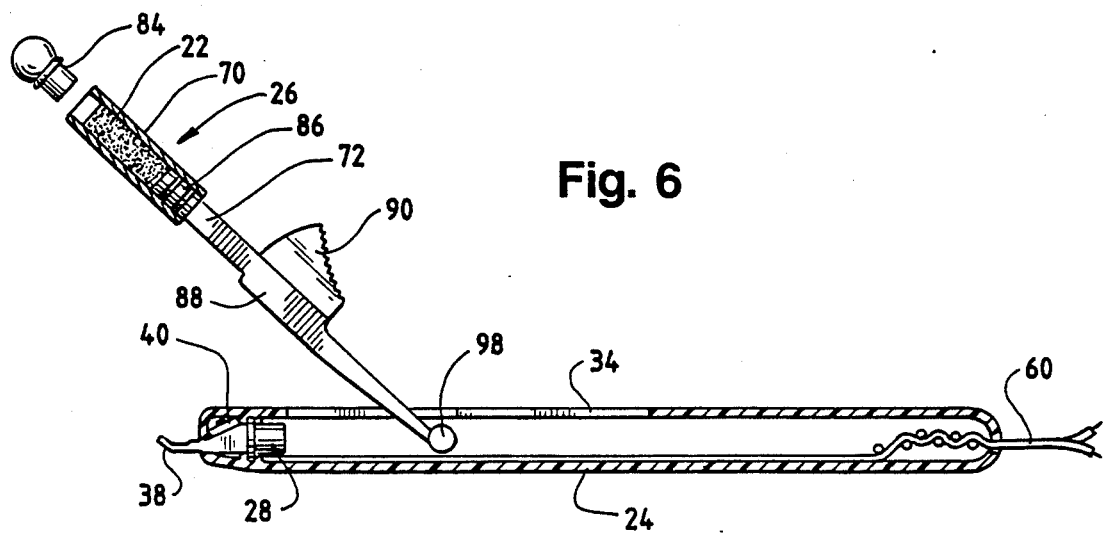
FIG. 6 is a partial sectional view of the bioadhesive applicator, with the adhesive cartridge assembly in the preparatory position for insertion into the applicator housing.

While the invention may be susceptible to embodiment in different forms, there is shown in the drawings, and herein will be described in detail, a specific preferred embodiment with the understanding that the present disclosure is to be considered an exemplification of the principles of the invention, and is not intended to limit the invention to the embodiment as illustrated and described herein.

a Bioadhesive applicator 20 that is used for dispensing a metal adhesive material 22 is generally illustrated in the FIGS. The adhesive material 22 is viscous, and upon heating becomes less viscous and can flow under suitable pressure and direction. As noted above, the adhesive material is used to close a surgical incision. A typical application for the adhesive 22 would be to bond the incised cornea tissue back down at the cornea/sclera incision commonly made for interocular (I.O.L.) lens insertion. Preferably, the adhesive 22 is applied along a 0.120–0.190 inch wide strip and 0.002 inch thickness in order to properly seal the incision.

As discussed above, the adhesive at room temperature is rather viscous and of a gel-like consistency. At approximately 55°–60° C. the adhesive will melt or become less viscous, retaining a rubbery consistency and tends to resolidify at 40° 42° C. The challenge of the present invention is to maintain the melted or less viscous state for the adhesive prior to and during application and to prevent cooling thereof which results in the bioadhesive material reforming as a bead, rather than remaining in an applied strip. With the applicator 22 to be described, the adhesive material is applied by a heated end which includes a spatula-like applicator tip. The applicator tip will flatten or spread the droplet of adhesive material under the tip such that the adhesive can be spread in a thin strip of desired width until the droplet is consumed. The thickness of the strip is controlled by the surgeon and the amount of pressure applied and speed of application. The particular adhesive with which the applicator is designed to be used is proprietary, but retains sufficient period of tackiness to permit the surgeon to adjust the position of the tissue before the adhesive sets.

As illustrated in FIG. 2, the bioadhesive applicator 20 generally includes a housing 24, an adhesive cartridge assembly 26, and a heat sink and tip assembly 28. The housing 24 may take one of many forms. In the preferred embodiment, the housing 24 is an elongated, generally cylindrical, hollow member that receives the adhesive cartridge assembly 26 and heat sink and tip assembly 28 therein. The housing's cylindrical shape will allow a surgeon to easily hold the bioadhesive applicator 20 in his/her hand. The housing 24 includes an aperture 30 or 32 at each end, as clearly shown in FIG. 2, and a slot 34 along the topmost area, as clearly shown in FIG. 1, whose function will be described hereinafter. The housing 24 is made of a suitable material such as plastic or the like.

The heat sink and tip assembly 28 is fixedly attached to the housing 24 in the preferred, illustrated embodiment will be described in detail. As clearly shown in FIG. 3, the heat sink and tip assembly 28 generally includes an enlarged heat sink portion 36, an applicator tip 38 and a positive temperature coefficient (PTC) heater element 40. PTC heater elements are well known in the art and in effect are self-regulating heaters that will reach a desired, predetermined temperature and will maintain that temperature as long as a current path is established. The enlarged heat sink portion 36 has a tapered end portion that terminates in a substantially planer end face 46. The end face 46 will abut and engage the adhesive material prior to heating as will be described. When the PTC element 40 is energized, heat is applied to the rather viscous bioadhesive material in proximity to the end face 46 causing this material to melt or become less viscous, so that it can be extruded through the enlarged heat sink portion 36 and the applicator tip 38 by means of a through bore 44, as explained hereinafter. More specifically, the heat sink 36 melts the adhesive material 22 which travels through the heat sink 36 as pressure is applied by the applicator 20, as described herein, and forms a spherical droplet on the tip 38. This droplet may then be spread over the tissue surfaces to be adhered by using the applicator tip 38. As shown in FIG. 2, the heat sink and tip assembly 28 is attached to a front end 42 of the housing 24.

In the preferred embodiment, and as shown in FIG. 3, the heat sink 36 and applicator tip 38 are constructed as a single piece. However, it is to be understood that the heat sink 36 and tip 38 may be formed as separate elements which are attached by appropriate means such as bonding or insert molding the tip 38 into the heat sink 36.

In the preferred, illustrated embodiment, the heat sink and tip assembly 28 is heat conductive and made of a suitable material such as metal or the like. It to be understood that the material that is used for the heat sink and tip assembly 36 must be able to distribute the heat generated from the PTC heater element 40 uniformly throughout the entire heat sink and tip assembly 28 in order to assure that the adhesive material 22 remains melted or in a reduced viscosity state.

As clearly shown in FIG. 3, a bore 44 extends through the entire heat sink and tip assembly 28 from the rearmost end face 46 of the heat sink 36 to the frontmost end portion 48 of the applicator tip 38. This bore 44 enables the melted adhesive 22 to be extruded from the cartridge assembly 26 out onto the applicator tip 38, for application to the surface area of the incision. As shown in FIGS. 4 and 5, the bore 44 is of a minute diameter in order to allow only a small amount of melted adhesive 22 to pass through at a time. The minute diameter of the bore 44 and the physical pressure that is applied to the applicator 20 controls the droplet size that is formed on the tip 38. Furthermore, the minute diameter of the bore 44 minimizes the amount of drooling or dripping of the adhesive which must be controlled for proper application. In the preferred embodiment, the bore 44 has a diameter of 0.013 inches or less which has been found to provide the desired results.

The heat sink 36 will now be discussed in detail. The heat sink 36 melts or reduces the viscosity of the adhesive material 22 that is located in the adhesive cartridge assembly 26. The heat sink 36 may take one of many forms so long as it is completely enclosed within the housing 24. In the preferred embodiment, as best shown in FIG. 3, the heat sink 36 has a tapered rear section 50, a body portion 52 and a sloped front section 54.

The tapered rear section 50 is generally of a cylindrical configuration that has a gradually decreasing diameter from front to back. The tapered rear section 50 facilitates attachment of the cartridge assembly 26, and provides a tapered, friction fit and seal. The sloped front section 54 slopes from back to front and terminates at the applicator tip 38.

In order to mount the heat sink and tip assembly 28 within the housing 24, the body 52 includes an annular rib 56 which is received within a corresponding groove 58 in the housing 24. Thus, the heat sink and tip assembly 28 is securely held within the housing 24.

In the preferred embodiment, the PTC heater element 40 is mounted to the sloped front section 54 of the heat sink 36. The PTC heater element 40 is of a construction well known in the art and will not be described in detail herein. The PTC heater element 40 is used to uniformly heat the entire heat sink and tip assembly 28. The PTC heater element 40 is electrically activated and self-regulating. Electrical leads 60 are fed through the aperture 32 at the rear end 62 of the housing 24 and are connected to the PTC heater element 40 by known means and supply the necessary electrical power to the PTC heater element 40.

The construction of the applicator tip 38 is important to the proper application of the bioadhesive material and will now be described in detail. The applicator tip 38 is used to spread a thin layer of melted adhesive material 22 onto the surface area of the incision in order to close the incision. The tip 38 protrudes from the main body portion 36 of the heat sink and also extends outwardly from the applicator housing 24 through the aperture 30 in the front end 42 of the housing 24. After the adhesive 22 has been heated to reduce its viscosity and extruded through the aperture 44 to form a droplet on the tip 38, the adhesive 22 has a very rubbery consistency and prefers to reform immediately after extrusion into a bead. In order to overcome this problem, the applicator tip 38 includes a spatula-like end 64 which allows the user to spread a layer of adhesive 22 onto the surface area of the incision. The adhesive 22 is heated continuously as it passes from the adhesive cartridge assembly 26 through the bore 44 and out of an adhesive outlet hole 66 on to the applicator tip 38. The melted adhesive 22 forms a droplet on the applicator tip 38 which continues to apply heat to the adhesive. The spatula-like end 64 may include a hollowed out reservoir area 68 (dotted outline, FIG. 4) around the adhesive outlet hole 66, in order to form a larger droplet initially. A larger droplet may be needed, if a specific application so requires. When the melted adhesive 22 passes out of the adhesive outlet 66, the melted adhesive 22 will fill the hollowed out area 68 and form a larger droplet. The hollowed out area 68 will prevent the adhesive 22 from overspreading beyond the edges of the tip 38 when the tip 38 is initially applied to the surface area of the incision.

The spatula-like end 64 is employed by the surgeon to place droplet of adhesive in contact with the surface area of the incision, the spatula-like end 64 flattens out the droplet whereupon it spreads under the applicator tip 38. As the surgeon draws the tip 38 across the surface area of the incision, the adhesive 22 is spread evenly upon the axis of travel until the droplet has been consumed. The pressure applied and the speed of movement will control the thickness of the layer applied, the width of this layer is determined by the spatula dimension.

Attention is now directed to the adhesive cartridge assembly 26. The adhesive cartridge assembly 26 is a separate component or assembly from the applicator housing 24 and heat sink and tip assembly 28 and contains a quantity of unmelted adhesive material 22 and it also allows the surgeon to dispense the adhesive material 22, once the viscosity of the adhesive 22 has been reduced by the heat sink 36. As shown in FIG. 6, initially, the cartridge assembly 26 is separate from the housing 24 and heat sink and tip assembly 28. As shown in FIG. 2, the adhesive cartridge assembly 26 is generally comprised of an adhesive chamber 70 for holding the adhesive material 22, and a plunger member 72.

The adhesive chamber 70 includes a hollow cylindrical housing 74 with an opening 76,78 at each end 80, 82, which defines an internal bore in which the adhesive 22 is disposed. As shown in FIG. 6, initially, in order to insure the sterility of the adhesive material 22, the adhesive chamber 70 includes a stopper or insert 84 at the frontmost end 80 which must be removed before the cartridge assembly 26 is inserted into the housing 24. The stopper 84 is shown as a separate removable and discardable element. It may, however, be molded integral with the housing 70.

The chamber housing 74 holds the adhesive material 22 therein. The chamber housing 74 has an outer diameter that is smaller than the internal diameter of the elongated housing 22, thus permitting when the chamber housing 74 to be inserted easing into the elongated housing 22. The front opening 76 of the chamber housing 74 has a diameter that is slightly larger than the largest diameter of the tapered rear section 50 of the heat sink 36. Thus, when the adhesive cartridge assembly 26 is inserted into the housing 22, (the insert or stopper 84 having been removed) the rearmost end of the conical rear section 50 will be accepted into the opening 76 to provide a sealed friction fit. Furthermore, the tapered or conical shape of the rear section 50 will facilitate the entry of the rear section 50 into the chamber housing 74.

The plunger member 72 is used to pressurize the adhesive material 22 and force it against the heat sink 36 so it can be heated and the viscosity thereof reduced as the surgeon applies continuous pressure to the plunger assembly 72, the melted adhesive 22 is extruded through the heat sink and tip assembly 28. The plunger assembly 72 generally includes a piston-like head portion 86, an elongate shaft or extension 88 and a finger engaging portion 90.

The piston-like head 86 of the plunger assembly 72 is inserted into the rear opening 78 of the chamber housing 74 and abuts a rear end of the adhesive material 22. The outer diameter of the piston 86 achieves a sliding, friction fit with the internal diameter of the chamber housing 74. Thus, the head 86 can slide within the chamber housing 74 in order to apply pressure to the adhesive material 22 forward. A frictional coefficient between the inside wall 92 of the chamber housing 74 and the exterior of the piston 86 holds the head 86 securely within the chamber housing 74. The piston 86 is preferably formed integral with the remainder of the plunger member 72, the entire member being molded of a thermoplastic material, in the preferred illustrated embodiment. The piston 86 includes a pair of grooves 94 to provide a labyrinth type seal to prevent any adhesive material 22 from passing between the piston 86 and interior chamber wall 92.

Extending from the rear end 96 of the piston-like head 86 is an elongated shaft or extension 88. The shaft 88 includes a cylindrical cross-head 98 at the end opposite to the piston-like head 86. The cross-head 98 facilitates the entry of the cartridge assembly 26 into the housing 24 as will be described in detail herein. Also formed on the shaft or extension 88 is a finger portion 90 that extends outwardly from the housing 24 through the elongated slot 34 in the applicator 20. The finger portion 90 allows the surgeon to advance the plunger assembly 72 manually within the cartridge assembly 26 by applying pressure thereto. The finger portion 90 is ridged so that the surgeon's finger will not slip off of it when the surgeon is applying pressure.

Having disclosed the specifics and overall construction of the bioadhesive applicator 20, a method for assembling and using the applicator 20 will now be discussed.

Figure 7:
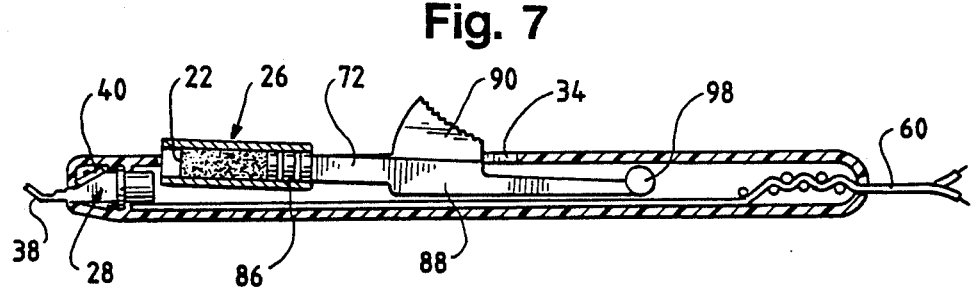
FIG. 7 is a partial sectional view of the bioadhesive applicator and the adhesive cartridge in a partially assembled condition.
Figure 8:
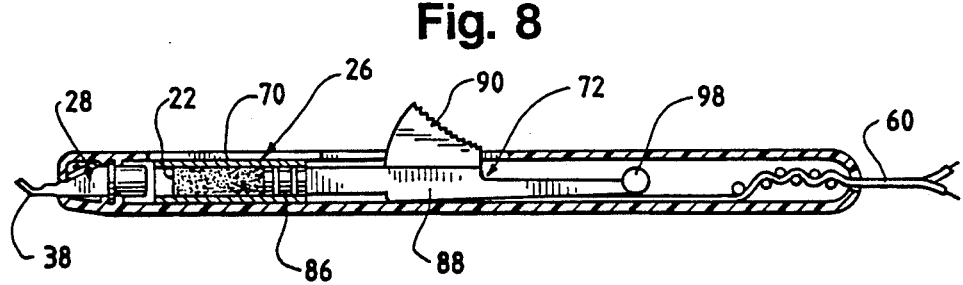
FIG. 8 is a partial sectional view of the bioadhesive applicator and the adhesive cartridge in a partially assembled condition prior to advancement of the cartridge plunger to attain the condition as shown in FIG. 2.

Turning to FIGS. 6–8, initially, the adhesive cartridge assembly 26 is separate from the housing 24 and heat sink and tip assembly 28. Immediately prior to assembly, the user removes the insert or stopper 84 from the cartridge assembly 26. Next, as shown in FIG. 6, the cross-head end 98 of the extension 88 is inserted into the housing 24 through the slot 34. As shown in FIG. 7, as the cross-head 98 slides along the interior 100 of the housing 24, the extension 88 and the chamber housing 74 follow through the slot 34. As shown in FIG. 8, the cross-head 98 continues to slide along the interior of the housing 24 until the entire cartridge assembly 26 is inserted fully into the housing 24 and the finger portion 90 contacts the rearmost end 102 of the slot 34. The finger portion 90 extends outwardly through the slot 34 in the topmost area of the housing 24. The cross-head portion 98 is sized and dimensioned so that it will engage the interior side walls of the housing 24. The circular, cross-sectional shape of the cylindrical cross-head 98 facilitated initial insertion and sliding movement as illustrated in FIGS. 6–8. The trans-axial extent of the cross-head 98 is such that its engagement or near engagement with the side walls of the housing 24 serves to position the cartridge assembly properly within the housing 24.

When the adhesive cartridge assembly 26 is fully inserted into the housing 24, the surgeon applies pressure upon the finger portion 90 in the forward direction. This pressure will cause the entire cartridge assembly 26 to move forward within the housing 24 toward the heat sink and tip assembly 28. As the surgeon applies continuous pressure, the front opening 76 of the adhesive chamber 70 contacts the tapered or conical rear section 50 of the heat sink 36. The conical rear section 50 then enters into the adhesive chamber 70 to provide a friction seal. When the conical rear section 50 is fully inserted into the chamber 70, the applicator 20 is fully assembled and is in the condition as shown in FIG. 2.

Once the applicator 20 is fully assembled, the applicator 20 is ready for use. The PTC heater element 40 is energized, or it may have been energized prior to insertion of the adhesive cartridge assembly, which results in the heat sink and tip assembly 28 being uniformly heated. The adhesive material 22 that abuts the heat sink 36 will melt or become less viscous. As the surgeon applies pressure onto the finger portion 90 in order to advance the plunger assembly 72 forward within the chamber housing 74 this causes the melted adhesive 22 to enter into the bore 44. As the surgeon applies continuous pressure, the adhesive material 22 is extruded through the bore 44 to the applicator tip 38.

As the melted adhesive material 22 passes through the bore 44 and onto the applicator tip 38, the material 22 is subjected to heat since the entire heat sink and tip assembly 28 is heated. The melted material 22 exits out of the adhesive outlet hole 66 in the spatula-like end 64 of the tip 38 and forms a droplet.

The surgeon then places the spatula-like end 64 of the applicator 20 onto the surface area of the incision. The adhesive droplet is crushed or deformed under the pressure of the tip 38 and upon movement of the applicator by the surgeon, the droplet spreads under the tip 38. As the surgeon draws the tip 38 across the surface area of the incision, the adhesive 22 is spread along the axis of travel until the droplet has been consumed. Thickness of the deposited layer is controlled by the pressure and the speed that the surgeon draws the tip across the surface area of the incision. A longer band of adhesive can be applied if additional material is extruded simultaneously with the drawing operation or if a larger droplet is formed initially.

The embodiment of the present invention as illustrated and described herein is directed to a dispensable type applicator. That is, following initial use, both the housing 24, with its heat sink and tip construction 28, and the adhesive cartridge 26 are discarded. Toward this end, the various components and overall construction of the applicator 20 have been designed for thermoplastic molding and ease and simplicity in construction of the mold tooling. It is envisioned, however, that the applicator housing 24 with its heat sink and applicator tip 28 could be of reusable more permanent construction, with only the adhesive cartridge being disposable after use. Similarly, the unit could be designed so that only the adhesive chamber 70 is disposable. With the extension 88 and finger portion 90 being slidably mounted to the re-usable housing assembly. Thus, while a preferred embodiment of the present invention is shown and described, it is envisioned that those skilled in the art may devise various modifications of the present invention without departing from the spirit and scope of the appended claims. The invention is not intended to be limited by the foregoing disclosure.

The invention claimed is:

1. A bioadhesive applicator for use with an adhesive material for employment in a surgical procedure such as the sealing of an incision in an eye after surgery, to bond the cornea back down at the cornea/sclera incision commonly made for interocular lens insertion, said applicator being employable in closing said incision by spreading a thin layer of melted adhesive material onto the surface area of the incised tissue, said applicator including: a housing; a conductive heat sink located proximate an end of said housing, said heat sink including a bore therethrough; a heat conductive applicator tip operatively associated with said heat sink and extending outwardly from said housing, said tip having a bore therethrough in direct communication with said heat sink bore and said tip having a spatula-like end applicator portion through which said applicator tip bore opens; means providing a source of heat in operative control with said heat sink; an adhesive cartridge assembly positionable within said housing, said adhesive cartridge assembly including, an adhesive chamber for meltable adhesive material housed therein; a plunger member having one end in communication with said adhesive chamber and movable therein and including manually engageable means for effecting movement of said plunger member relative to said adhesive chamber, said adhesive chamber further being in communication with said heat sink wherein when said heat sink is heated, adhesive material in said chamber will melt and upon movement of said plunger, said melted adhesive is forced through the bores in said heat sink and tip in order to form a droplet on said applicator tip portion, and when said tip is placed on the surface area of an incision, melted adhesive is dispensed from said tip, and further when said spatula-like end is drawn across the surface area of the incision, the melted adhesive material is spread thereupon, said spatula-like end projecting from said tip bore at an angle relative to longitudinal dimension of said housing in order to promote application of pressure on said drawn spread of adhesive material across said incision surface area, said spatula-like end including a hollowed out area so that a larger drop of melted adhesive is formed on said tip.

2. An applicator as defined in claim 1, wherein said bores in said heat sink and tip each have a diameter equal to or less than approximately 0.013 inches.

3. An applicator as defined in claim 1, wherein said means providing a source of heat to said heat sink and tip are electrically provided by a PTC heating element which is in surface contact with said heat sink.

4. An applicator as defined in claim 1, wherein said housing includes a slot to allow the cartridge assembly to be inserted into the housing.

5. An applicator as defined in claim 4, wherein said plunger member of said adhesive cartridge assembly, includes an elongate axial extension received within said housing and having said manually engageable means formed thereon and extending outwardly of said housing through said slot.

6. An applicator as defined in claim 1, wherein said heat sink and said applicator tip are provided by a one-piece component with said applicator tip bore being an extension of said heat sink bore.

7. An applicator as defined in claim 1, wherein said means providing a source of heat is electrically energized, and power cord means for connecting the electrically energized heating means to a source of electrical power.

8. A bioadhesive applicator for use with an adhesive material for employment in a surgical procedure such as the sealing of an incision in an eye after surgery, to bond the cornea back down at the cornea/sclera incision commonly made for interocular lens insertion, said applicator being employable in closing said incision by spreading a thin layer of melted adhesive material onto the surface area of the incised tissue, said applicator including: a housing; a conductive heat sink located proximate an end of said housing, said heat sink including a bore therethrough; a heat conductive applicator tip operatively associated with said heat sink and extending outwardly from said housing, said tip having a bore therethrough in direct communication with said heat sink bore and said tip having a spatula-like end applicator portion through which said applicator tip bore opens; means providing a source of heat in operative control with said heat sink; an adhesive cartridge assembly positionable within said housing, said adhesive cartridge assembly including, an adhesive chamber for meltable adhesive material housed therein; an plunger member having one end in communication with said adhesive chamber and movable therein and including manually engageable means for effecting movement of said plunger member relative to said adhesive chamber, said adhesive chamber further being in communication with said heat sink wherein when said heat sink is heated, adhesive material in said chamber will melt and upon movement of said plunger, said melted adhesive is forced through the bores in said heat sink and tip in order to form a droplet on said applicator tip portion, and when said tip is placed on the surface area of an incision, melted adhesive is dispensed form said tip, and further when said spatula-like end is drawn across the surface area of the incision, the melted adhesive material is spread thereupon, said housing including a slot to allow the cartridge assembly to be inserted into the housing and said plunger member of said adhesive cartridge assembly, including an elongate axial extension received within said housing and having said manually engageable means formed thereon and extending outwardly of said housing through said slot, wherein said elongate axial extension terminates in a cylindrical cross-head that is received within the interior of said housing and engages the walls thereof to position said plunger therein.

9. A bioadhesive applicator for use with an adhesive material for employment in a surgical procedure such as the sealing of an incision in an eye after surgery, to bond the cornea back down at the cornea/sclera incision commonly made for interocular lens insertion, said applicator being employable in closing said incision by spreading a thin layer of melted adhesive material onto the surface area of the incised tissue, said applicator including: a housing; a conductive heat sink located proximate an end of said housing, said heat sink including a bore therethrough; a heat conductive applicator tip operatively associated with said heat sink and extending outwardly from said housing, said tip having a bore therethrough in direct communication with said heat sink bore wherein said heat sink and said applicator tip are provided by a one-piece component with said applicator tip bore being an extension of said heat sink bore, and said tip having a spatula-like end applicator portion through which said applicator tip bore opens; means providing a source of heat in operative control with said heat sink; an adhesive cartridge assembly positionable within said housing, said adhesive cartridge assembly including, an adhesive chamber for meltable adhesive material housed therein; wherein said heat sink includes an axial extension received within said adhesive chamber and providing an end face in heat conductive communication with the interior of said chamber, a plunger member having one end in communication with said adhesive chamber and movable therein and including manually engageable means for effecting movement of said plunger member relative to said adhesive chamber, said adhesive chamber further being in communication with said heat sink wherein when said heat sink is heated, adhesive material in said chamber will melt and upon movement of said plunger, said melted adhesive is forced through the bores in said heat sink and tip in order to form a droplet on said applicator tip portion, and when said tip is placed on the surface area of an incision, melted adhesive is dispensed form said tip, and further when said spatula-like end is drawn across the surface area of the incision, the melted adhesive material is spread thereupon.

10. An adhesive cartridge assembly for use with a bioadhesive applicator of the type employed to dispense an adhesive material for employment in surgical procedures, such as the closing of an incision in cornea tissue employed in interocular lens replacement, said cartridge being employable with an applicator having means for controlled dispensing of a bioadhesive, and also providing an elongate, hollow housing, said adhesive cartridge assembly including: an adhesive chamber for adhesive material disposed therein for dispensing, a removable and discardable stopper member for closing one end of the chamber; a plunger member having a piston-like end portion which end portion is disposed in the other end of the chamber; a plunger member having a piston-like end portion which end portion is disposed in the other end of said chamber for movement relative to said chamber to pressurize a quantity of bioadhesive material therein, and manually engageable means on said plunger member to effect the controlled movement of said plunger to force bioadhesive from said chamber to the applicator means for dispensing thereof, wherein said plunger includes an elongate extension having a cylindrical cross-head on the distal end thereof which is received within the applicator and engages the interior thereof to position said plunger properly and to facilitate engagement of said cartridge assembly within said applicator housing.

11. A cartridge assembly according to claim 10, wherein said plunger includes an elongate extension extending axially away from said piston-like end, a projection on said elongate extension adapted to extend externally of said applicator to provide said manually engageable means.

12. A cartridge assembly according to claim 10, in combination with a heat conductive applicator tip having a hollowed out area in flow communication with said adhesive chamber so that a larger drop of melted adhesive is formed on said tip.

13. A cartridge assembly according to claim 10, further comprising a heat sink including an axial extension received within said adhesive chamber and providing an end face in heat conductive communication with the interior of said chamber.

* * * * *